United States Patent [19]

Arai et al.

[11] Patent Number: 4,594,225
[45] Date of Patent: Jun. 10, 1986

[54] ELEMENTS FOR ANALYSIS OF CALCIUM

[75] Inventors: Kazumi Arai; Mikio Koyama; Kenichiro Okaniwa, all of Hino, Japan

[73] Assignee: Konishiroku Photo Industry Co., Ltd., Tokyo, Japan

[21] Appl. No.: 775,709

[22] Filed: Sep. 13, 1985

Related U.S. Application Data

[63] Continuation of Ser. No. 484,238, Apr. 12, 1983, abandoned.

[30] Foreign Application Priority Data

Apr. 13, 1982 [JP] Japan ................... 57-62219

[51] Int. Cl.$^4$ .................. G01N 21/78; G01N 33/52
[52] U.S. Cl. ..................... 422/56; 422/57; 436/79; 436/170
[58] Field of Search ............ 422/55, 56, 57, 58; 436/79, 169, 170

[56] References Cited

U.S. PATENT DOCUMENTS

| | | | |
|---|---|---|---|
| 3,798,000 | 3/1974 | Helger | 436/79 |
| 3,934,977 | 1/1976 | Cleaver | 436/79 X |
| 3,938,954 | 2/1976 | Stavropoulos et al. | 436/79 X |
| 3,992,158 | 11/1976 | Przybylowicz et al. | 422/57 |
| 4,050,945 | 9/1977 | Suzuki | 106/24 X |
| 4,066,403 | 1/1978 | Bruschi | 436/170 X |
| 4,144,306 | 3/1979 | Figueras | 436/170 X |
| 4,166,093 | 8/1979 | Smith-Lewis et al. | 422/56 |

FOREIGN PATENT DOCUMENTS 0149966  9/1982  Japan .................. 436/79

OTHER PUBLICATIONS

CRC Handbook of Chemistry and Physics, 1966–1967 47th Edition, p. D–80.

Primary Examiner—David L. Lacey
Assistant Examiner—Robert J. Hill, Jr.
Attorney, Agent, or Firm—Frishauf, Holtz, Goodman & Woodward

[57] ABSTRACT

An improved multilayer analytical element for the determination of calcium comprising a liquid impermeable, optically transparent support; at least one reagent layer positioned with a first side on said support and containing at least one reagent capable of reacting with a calcium component in a fluid sample; and at least one porous developing layer on the second side of said reagent layer, said porous developing layer being permeable to calcium from said fluid sample thereby transporting said calcium to said reagent layer. The improvement comprises at least one of said reagent layer and developing layer containing a basic substance of the formula $M_vH_wPO_4 \cdot ZH_2O$ wherein M is lithium, sodium or potassium; v is an integer of 2 or 3 and w is an integer of 0 or 1 provided that v plus w equals 3; and Z is ½ when M is lithium, 0, 2 or 12 when M is sodium and 0 or 8 when M is potassium; and said reagent layer contains (i) 3,3'-bis[N,N-di(carboxymethyl)aminomethyl]-o-cresolphthalein and (ii) 8-hydroxyquinoline or a derivative thereof.

15 Claims, No Drawings

ELEMENTS FOR ANALYSIS OF CALCIUM

This application is a continuation of application Ser. No. 484,238, filed Apr. 12, 1983, now abandoned.

BACKGROUND OF THE INVENTION

1. Field of the Invention

This invention relates to an analytical element for analytical chemistry, especially for analysis of the predetermined specific component in a fluid. More particularly, it is concerned with a quantitative analytical element for quantitative analysis of calcium in a biological fluid sample.

2. Description of the Prior Art

A number of methods for analysis of a component specimen in a fluid sample has been hitherto developed and roughly classified into two types, namely analysis reaction in a solvent system (hereinafter referred to as "wet chemistry") and analysis reaction in a solid phase system (hereinafter referred to as "dry chemistry").

The wet chemistry is known to include such analytical method as the so-called manual method without employing any device or apparatus up to the automatic quantitative analysis using a device or apparatus which have recently been employed in clinical test laboratories of hospitals.

As a determination method for calcium in a living body specimen according to the wet chemistry, there are mentioned a method with oxalate precipitation—potassium permanganate titration, the chelatometric titration method and the like.

The method with oxalate precipitation—potassium permanganate titration is to precipitate calcium as calcium oxalate, dissolve it in sulfuric acid and then determine the so-released oxalic acid according to calcium permanganate titration. However, this method has disadvantages of complicated procedures and inefficiency.

The chelatometric titration method is a method wherein calcium is converted to its chelate with ethylenediaminetetraacetic acid and the like and disappearance of calcium is determined from color change of an indicator to measure calcium concentration. However, this method requires complicated procedure in order to avoid influence of the co-existing magnesium and there is also a precision problem owing to the indirect determination of calcium concentration by back titration.

Generally speaking, the aforesaid methods have the disadvantages of complicated procedures, skilled operating techniques which are required and waste of time and labor.

On the other hand, the dry chemistry has been widely applied. For instance, the chemistry is conducted by impregnating a water absorbing carrier, e.g. a filter paper with an indicator solution followed by drying, as disclosed in U.S. Pat. Nos. 3,050,373, 3,061,523 and so on. Said method generally is to add a drop or drops of a fluid specimen to an analytical test paper or simply to a test strip or dip a test piece into a fluid specimen and to determine color change or density change in the test strip by visual observation or a reflection densitome, thereby measuring the concentration level of a specific component in a fluid sample.

These test methods are useful because of their simple procedures and results obtained in a short period of time, but they are not yet beyond the region of qualitative analysis, in view of a poor quantitativeness.

In contrast to the prior analytical methods as depicted above, there has been proposed an element for liquid analysis, as disclosed in U.S. Pat. No. 4,166,093, by the use of a conveniently operated dry chemistry with a high quantitative ability. This element is an analytical element which comprises a reagent layer placed over one side of an optically transmitting, liquid impermeable carrier or support and containing at least one reagent capable of reacting with a component in a fluid sample; a porous radiation blocking layer which transmits the said component in a fluid sample into the said reagent layer; and a radiation transmitting, detectable substance migration inhibiting layer interposed between the said two layers (U.S. Pat. No. 4,166,093).

According to the above-defined construction, calcium in a fluid sample can form a chelate with the indicator present in a reagent layer, for example, sodium 3,6-bis(4-chloro-2-phosphonophenylazo)-4,5-dihydroxy-2,7-naphthalenedisulfonate or 1,8-dihydroxynaphthalene-3,6-disulfonic acid-2,7-bis(azo-2-phenylarsonic acid) and the like with coloration. This method, unlike the wet chemistry, is convenient and quantitative generally to divalent metal ions, but has the great disadvantage of poor specificity to calcium with a remarkably lowered precision in calcium quantitative determination.

Moreover, the analytical element using 1,8-dihydroxynaphthalene-3,6-disulfonic acid-2,7-bis(azo-2-phenylarsonic acid) as disclosed in the above U.S. patent may show absorbance up to around 650 nm, while calcium concentration is determined upon absorbance at 680 nm produced when the said acid forms a chelate with calcium, and thus there is the disadvantage of a large error produced from some shifts of measurement wave length.

SUMMARY OF THE INVENTION

As a result of our earnest studies to eliminate or diminish the aforesaid disadvantage, we have successfully accomplished the present invention, the improved analytical element having the following construction without the aforesaid disadvantages.

More specifically, these disadvantages can be eliminated or diminished by the use of a multilayer analytical element for the determination of calcium comprising a liquid impermeable, optically transparent support; at least one reagent layer having a first side on said support capable of reacting with a component in the fluid sample; and at least one porous developing layer located on the second side of said reagent layer which functions to transmit a component of a fluid sample to said reagent layer, characterized in that a basic substance having the general formula (I)

$$M_vH_wPO_4 \cdot ZH_2O \qquad (I)$$

wherein M is lithium, sodium or potassium; v is an integer of 2 or 3 and w is an integer of 0 or 1 provided that v plus w equals 3; and Z is ½ when M is lithium, 0, 2 or 12 when M is sodium, and 0 or 8 when M is potassium, is contained in at least one of said reagent layer and developing layer and 3,3'-bis[N,N-di(carboxymethyl)aminomethyl]-o-cresolphthalein and 8-hydroxyquinoline or a derivative thereof are contained in said reagent layer.

DETAILED DESCRIPTION

The calcium detection reaction in this invention is to determine the calcium concentration through chelate formation of 3,3'-bis[N,N-di(carboxymethyl)aminomethyl]-o-cresolphthalein with calcium. However, calcium is usually not present alone in a biological fluid sample such as blood, urine, lymph and the like. Namely, it is obvious that there exist alkaline earth metals analogous to calcium. In particular, it is well-known that magnesium tends to induce competitive inhibition to calcium detection reaction when determined and to give positive errors.

In order to eliminate such positive errors caused by the presence of magnesium, a magnesium shielding agent, i.e. 8-hydroxyquinoline or derivatives thereof are present together with the said compound and the reaction condition is kept basic, whereby the calcium concentration can be determined with greater precision. However, it is well-known in the photographic art that it is usually difficult to incorporate an alkali into a dry coating film for maintaining the reaction condition basic. Namely, incorporation of an alkali into a binder for film formation may cause deterioration of binder properties together with adverse influences to other layers.

Nevertheless, it becomes possible to make the pH within the layers alkaline without any adverse influences to the film by the use of the present basic substance.

The basic substance which may be employed in this invention is selected from phosphoric acid double (dibasic) salts and phosphoric acid triple (tribasic) salts as represented by the above general formula (I).

Illustrative examples of the basic substance in this invention are recited below, but are not contemplated to limit the present invention thereto.

(1) $Li_3PO_4 \cdot \frac{1}{2}H_2O$
(2) $Na_2HPO_4$
(3) $Na_2HPO_4 \cdot 2H_2O$
(4) $Na_2HPO_4 \cdot 12H_2O$
(5) $Na_3PO_4 \cdot 12H_2O$
(6) $K_2HPO_4$
(7) $K_3PO_4$
(8) $K_3PO_4 \cdot 8H_2O$ Of the above-illustrated compounds, those basic substances wherein the metal is potassium or sodium are particularly preferable and any salt form of the phosphoric acid double and triple salts may be preferably employed.

The present basic substance does not form a buffering agent, nor shows any buffering action. More specifically, a buffering agent is usually meant to indicate a mixture of a base or an acid with a salt, but the present substance consists of a basic substance only and obviously does not show any buffering action. Namely, if an equivlent of an acid is added, the hydrogen ion concentration (called pH) changes to neutral without maintaining a constant pH value.

The present compound is incorporated into an analytical element in order to keep the pH of the analytical element under a highly alkaline condition.

For the present analytical element, the basic substance is satisfactorily added in such an amount that the pH of said element may be kept in the range of about 9.0 to 13.5 when said sample is to be applied, more preferably the amount should be so as to keep the pH at about 9.5 to 12.5.

The present basic substance may be dispersed or dissolved in a variety of binders. As the binders, there may be mentioned, for instance, styrene and its derivatives, e.g. polystyrene and the like; a polyacrylic acid ester, e.g. polyacrylic acid methyl ester, polyacrylic acid ethyl ester and the like; a polymethacrylic acid ester, e.g. polymethacrylic acid methyl ester, polymethacrylic acid ethyl ester and the like; a polyvinyl heterocycle, e.g. polyvinyl pyrrolidone and the like; a synthetic polymer and its copolymers, e.g. polyvinyl butyral, polyacrylamide, polyvinyl acetate partial hydrolyzate, polyvinyl alcohol and the like; a natural polymer and its derivatives such as a gelatin, e.g. gelatin, a gelatin derivative and the like; a cellulose derivative, e.g. ethylcellulose, hydroxyethylcellulose, dacetylcellulose and the like.

The present basic substance can be dispersed or dissolved in a solution containing the above binder in an organic solvent or water, divided, for example, by means of a ball mill and then coated.

In a solution or dispersion containing the said binder, the present basic substance may be added at a concentration of the maximum 100% by weight to the binder and, desirably, at any optional concentration, preferably up to 80% by weight at the maximum.

The present basic substance may be incorporated into at least any one of the reagent layer and the porous developing layer. In the case wherein the basic substance is to be added to the reagent layer, another reagent of this invention, namely 3,3'-bis[N,N-di(carboxymethyl)aminomethyl]-o-cresolphthalein and 8-hydroxyquinoline or its derivative may be incorporated into the same reagent layer or, alternatively, may be incorporated into respective separate layers.

In the particular case wherein the present basic substance and other reagents are to be employed in separate layers, other reagents may be incorporated into the first reagent layer from the side of a support and the basic substance into the second reagent layer or the reverse may be also feasible favourably for the present multilayer analytical element.

In the case of separate layers employed as depicted above, the binder preferably employed for the layer containing 3,3'-bis[N,N-di(carboxymethyl)aminomethyl]-o-cresolphthalein and 8-hydroxyquinoline or its derivative may include, for example, a gelatin derivative such as gelatin or phthalated gelatin, a hydrophilic colloidal substance such as polyvinyl alcohol, polyvinyl pyrrolidone, polyacrylamide and the like.

The 8-hydroxyquinoline and its derivatives are represented by the following general formula (II)

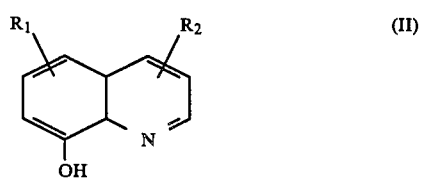

wherein $R_1$ and $R_2$ may be the same or different and each may be a hydrogen atom, a substituted or unsubstituted lower alkyl group of 1 to 4 carbon atoms, an aryl group, a sulfonic acid or sulfonate group or a halogen atom.

Preferably, there may be mentioned

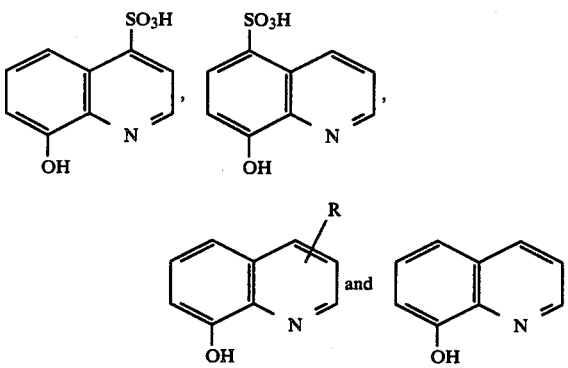

(wherein R is, for example, a halogen atom such as chlorine, bromine or the like and substitued at the 3-,4-,5-,6- or 7-position).

The porous developing layer in this invention may be optionally selected from those having performances as described in Japanese Patent Publication No. 21677/1978, namely, (1) to uniformly distribute a certain volume of a fluid sample over the reagent layer at a certain amount per unit area, (2) to remove any substance or factor capable of inhibiting an analytical reaction in a fluid sample and (3) to conduct a background action for reflecting a measured light transmitted through a support when spectrophotometric analysis is to be effected. Therefore, the present developing layer may exert all three functions as described above or, alternatively, the three functions may be properly separated and separate layers may be employed for respective functions. Moreover, it is feasible to use a layer having any two functions among the above three functions and another layer having the remaining function in combination. For example, there may be mentioned the non-fibrous, porous medium developing layer called "brush polymer" consisting of titanium dioxide and cellulose diacetate as disclosed in the above-defined Patent Publication; such fibrous developing layers as disclosed in Japanese Provisional Patent Publication No. 24576/1981, our co-pending Japanese Provisional Patent Publications No. 125847/1982 and No. 197466/1982 and so on. Especially, the said fibrous developing layer is particularly useful as a material capable of transferring the blood cell portion rapidly.

Further, the present basic substance, as explained hereinabove, may be incorporated into the said porous developing layer. Incorporation may be accomplished in the same manner as described above.

The aforesaid liquid impermeable, optically transmitting support for the present analytical element (hereinafter referred to as the present support) may be any kind, if it is liquid impermeable and optically transparent. Various polymeric materials such as cellulose acetate, polyethylene terephthalate, polycarbonate or polystyrene and inorganic materials such as glass may serve this usage purpose. In this instance, a thickness of the present support is not critical, but preferably from about 50μ to 250μ.

Other additives such as a buffering agent, a preservative, a surface active agent and the like may be also incorporated into each layer in the present multilayer analytical element as desired for purposes.

Particularly, a surface active agent may be effectively applicable for control of permeation ratio and others when a fluid sample is applied to the present element. As the surface active agent employable for this purpose, there may be used any of ionic (i.e. cationic or anionic) and nonionic surface active agents. Nonionic surface active agent may be preferably and effectively employed. As examples of nonionic surface active agent, there may be mentioned, for example, a polyalkylene glycol derivative of an alkyl-substituted phenol, e.g. 2,5-di-tert-butylphenoxypolyethylene glycol, p-octylphenoxypolyglycidyl ether and the like; a polyalkylene glycol ester of a higher fatty acid; and the like. Such surface active agent may control the permeation ratio of a fluid sample into the reagent layer and, simultaneously, inhibit undesirable development of "chromatographic phenomenon". Also, the surface active agent may diminish various, unfavourable influences due to proteins contained in the biological fluid sample.

The surface active agent may be employed at a widely selected ratio, but it may be employed at 10% by weight to 0.005% by weight upon the weight of a binder, preferably 6% by weight to 0.05% by weight.

Further, one side to be observed in the present support may be optionally processed according to the desired purpose. Also, an optically transparent subbing layer may be applied onto the present support at the side which the reagent layer is to be laminated, if desired, in order to improve adhesion between the reagent layer and the present support.

The present reagent layer including other layers may be coated over the present support by means of various coating methods, for instance, the dip-coating method, the air-knife method, the curtain coating method, and the extrusion coating method using a hopper as disclosed in U.S. Pat. No. 2,681,249 and the like. Alternatively, two or more layers, as desired, may be coated thereover simultaneously by a method as disclosed in U.S. Pat. No. 2,761,791 and British Pat. No. 837,095.

The drying temperature for the present reagent layer is not critical because no enzyme is used therein and, for instance, a wide range of temperature from room temperature to about 100° C. may be suitably applied.

The present multilayer analytical element may be of various different configurations. Also, any analytical element for the present purposes may be assembled by combining the present reagent layer with various functional layers, reagent-containing layers and members; for example, the reagent layer, the reflecting layer and the subbing layer as disclosed in U.S. Pat. No. 3,992,158; the radiation blocking layer as disclosed in U.S. Pat. No. 4,042,355; the barrier layer as disclosed in U.S. Pat. No. 4,066,403; the registration layer as disclosed in U.S. Pat. No. 4,144,306; the migration inhibiting layer as disclosed in U.S. Pat. No. 4,166,093; the scintillation layer as disclosed in U.S. Pat. No. 4,127,449; the cleaning layer as disclosed in Japanese Patent Provisional Publication No. 90859/1980; the breaking pod-like member as disclosed in U.S. Pat. No. 4,110,097; and the like.

The analytical element of this invention may be applicable to colorimetric determination by reflective spectrophotometry. Thus, the calcium concentration level can be determined by measurement of reflection absorbance at 575 nm.

In the present analytical element as constructed above, a fluid sample is fed from the developing layer side, a reflection density is measured by observation of analytical reaction in the reagent layer from the transparent support side and the so obtained measurement is referred to a previously prepared calibration curve to determine an amount of the unknown test substance.

The amount of the fluid sample to be applied to the present analytical element is not critical, but about 50 μl of the sample is preferable, more preferably about 20 μl to 5 μl. It is usually preferred to apply about 10 μl of a fluid sample.

The analytical element of this invention may be employed for quantitative determination of calcium that would be present in a wide variety of fluid samples. Typically, the present element may be useful in the field of clinical chemistry and employable for analysis of, particularly, biological fluid samples, e.g. urea and derivatives thereof in blood (whole blood, plasma, serum), urine or cerebrospinal fluid.

This invention will be more fully illustrated by way of the following example, but they are not contemplated to be limiting the scope of this invention thereto.

EXAMPLE 1

The following layers having the under-mentioned formulations were in turn coated over a clear undercoated polyethylene terephthalate support with a film thickness of 180μ to prepare a multilayer analytical element (Analytical element-1).

(1) Reagent Layer:
Polyvinyl pyrrolidone: 21.5 g/m$^2$
Illustrated Compound No. 5: 74.9 g/m$^2$
8-Hydroxyquinoline: 1.6 g/m
3.3'-Bis[N,N-di(carboxymethyl)-aminomethyl]-o-cresol-phthalein: 0.81 g/m$^2$
Polyoxyethylene lauryl ether [Kao-Atlas Co., Ltd., Trade name "Emalgen 120"]: 0.8 g/m$^2$ A reagent layer with a dry film thickness of about 31μ composed of the above components.

(2) Fibrous developing layer:
Powdery filter paper (C) (Toyo Roshi K.K., 300 mesh or finer): 91 g/m$^2$
Copoly(styrene-glycidylmethacrylate) (a weight ratio of 95:5): 13.0 g/m$^2$
Polyoxyethylene lauryl ether [Kao-Atlas Co., Ltd., Trade name "Emalgen 120"]: 0.3 g/m$^2$ A developing layer with a fibrous structure and a dry film thickness of about 160μ composed of the above components.

Also, a comparative multilayer analytical element was prepared according to the same procedures as above except that the Illustrative Compound No. 5 of this invention was omitted.

For the above-mentioned present analytical element and comparative analytical element, serum models comprising a 5% bovine serum albumin solution in water containing calcium at respective concentrations of 1, 2, 5, 8, 10, 12 and 16 mg/dl and magnesium at a concentration of 2 mg/dl were prepared and 10 μl of each serum model were added dropwise to the fibrous developing layer of each of the said present analytical element and comparative analytical element. Then, incubation was effected at 37° C. for 10 minutes and reflection density was measured at 575 nm. The results are summarized in the following Table 1.

TABLE 1

| Ca concentration in serum model | Reflection density (575 nm) | |
|---|---|---|
| | Present analytical element-1 | Comparative analytical element-1 |
| 1 | 0.36 | 0.67 |
| 2 | 0.44 | 0.65 |
| 5 | 0.76 | 0.97 |
| 8 | 0.96 | 1.20 |
| 10 | 1.15 | 1.05 |
| 12 | 1.26 | 1.05 |

TABLE 1-continued

| Ca concentration in serum model | Reflection density (575 nm) | |
|---|---|---|
| | Present analytical element-1 | Comparative analytical element-1 |
| 16 | 1.46 | 1.17 |

As apparent from the above results, no correlation with Ca concentration in serum model was observed in the comparative analytical element owing to influence with the co-existing magnesium, whereas an extremely favourable correlation with the Ca concentration was observed in the present analytical element.

EXAMPLE 2

Analytical element-2 was prepared in the same manner as in Example 1 except that 16 g/m$^2$ of carboxymethylcellulose was used in place of the polyvinyl pyrrolidone in the reagent layer of Example 1 and that 35.5 g/m$^2$ of Illustrated Compound No. 7 was used in place of Illustrated Compound No. 5.

On the other hand, Comparative analytical element-2 in which Illustrated Compound No. 7 was excluded from Analytical element-2 was prepared in the same manner as in the above.

With respect to the respective Analytical element-2 and Comparative analytical element-2 thus prepared, reaction was conducted in the same manner as in Example 1 and reflection density was measured at 575 nm. The results are shown in Table 2.

TABLE 2

| Ca concentration in serum model | Reflection density (at 575 nm) | |
|---|---|---|
| | Present analytical element-2 | Comparative analytical element-2 |
| 1 | 0.45 | 0.51 |
| 2 | 0.57 | 0.60 |
| 5 | 0.77 | 0.79 |
| 8 | 0.95 | 0.96 |
| 10 | 1.05 | 1.08 |
| 12 | 1.16 | 1.12 |
| 16 | 1.28 | 1.23 |

EXAMPLE 3

Analytical element-3 was prepared in the same manner as in Example 1 except that 13 g/m$^2$ of hydroxymethylcellulose was used in place of the polyvinyl pyrrolidone in the reagent layer of Example 1 and that 24.7 g/m$^2$ of Illustrated Compound No. 1 was used in place of Illustrated Compound No. 5.

On the other hand, Comparative analytical element-3 in which Illustrated Compound No. 1 was excluded from Analytical element-3 was prepared in the same manner as in the above.

With respect to the respective Analytical element-3 and Comparative analytical element-3 thus prepared, reaction was conducted in the same manner as in Example 1 and reflection density was measured at 575 nm. The results are shown in Table 3.

TABLE 3

| Ca concentration in serum model | Reflection density (at 575 nm) | |
|---|---|---|
| | Present analytical element-3 | Comparative analytical element-3 |
| 1 | 0.60 | 0.57 |
| 2 | 0.63 | 0.59 |
| 5 | 1.00 | 0.96 |
| 8 | 1.10 | 1.05 |
| 10 | 1.10 | 1.00 |

TABLE 3-continued

| Ca concentration in serum model | Reflection density (at 575 nm) | |
|---|---|---|
| | Present analytical element-3 | Comparative analytical element-3 |
| 12 | 1.05 | 1.02 |
| 16 | 1.12 | 1.09 |

What is claimed is:

1. In an improved multilayer analytical element for the determination of calcium comprising;

a liquid impermeable, optically transparent support;

a reagent layer having first and second sides positioned with said first side on said support and containing at least one reagent capable of reacting with a calcium component in a fluid sample; and a porous developing layer on said second side of said reagent layer, said porous developing layer being permeable to calcium from said fluid sample thereby transporting said calcium to said reagent layer, the improvement comprising;

at least one of said reagent layer and developing layer containing a basic substance of the formula

wherein M is lithium, sodium or potassium; v is an integer of 2 and 3 and w is an integer of 0 or 1 provided that v plus w equals 3; and Z is ½ when M is lithium, 0, 2 or 12 when M is sodium and 0 or 8 when M is potassium; and said reagent layer contains (i) 3,3'-bis[N,N-di(carboxymethyl)aminomethyl]-o-cresolphthalein and (ii) 8-hydroxyquinoline or a derivative thereof.

2. The element of claim 1, wherein M is potassium or sodium.

3. The element of claim 1, wherein said derivative of 8-hydroxyquinoline is
8-hydroxyquinoline-4-sulfonic acid,
8-hydroxyquinoline-5-sulfonic acid
or a compound of the formula:

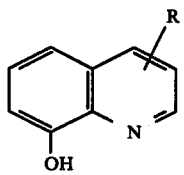

wherein R is a halogen atom positioned at the 3-, 4-, 5-, 6- or 7-position.

4. The element of claim 1, wherein said basic substance is contained in said reagent layer.

5. The element of claim 1, wherein said basic substance is dispersed or dissolved in a binder.

6. The element of claim 1, wherein said basic substance is $Na_3PO_4.12H_2O$.

7. The element of claim 1, wherein said basic substance is selected from the group consisting of $Li_3PO_4.\frac{1}{2}H_2O$, $Na_2HPO_4$, $Na_2HPO_4.2H_2O$, $Na_2HPO_4.12H_2O$, $Na_3PO_4.12H_2O$, $K_2HPO_4$, $K_3PO_4$ and $K_3PO_4.8H_2O$.

8. The element of claim 7, wherein said derivative of 8-hydroxyquinoline is
8-hydroxyquinoline-4-sulfonic acid,
8-hydroxyquinoline-5-sulfonic acid
or a compound of the formula:

wherein R is a halogen atom positioned at the 3-, 4-, 5-, 6- or 7-position.

9. The element of claim 8, wherein said reagent layer contains said basic substance and a binder.

10. The element of claim 8, wherein said basic substance is a potassium or sodium compound.

11. The element of claim 10, wherein said reagent layer contains said basic substance and a binder.

12. The element of claim 10, wherein said basic substance is in a layer comprising said basic substance and a binder and the pH of the analytical element is between about 9.5 and 12.5.

13. The element of claim 12, wherein said basic substance and said binder are contained in said reagent layer.

14. The element of claim 12, wherein said layer containing said binder and said basic substance also contains a surface active agent in an amount between 0.05% and 6% by weight of said binder.

15. The element of claim 14, wherein said basic substance and said binder are contained in said reagent layer.

* * * * *